| United States Patent [19] | [11] | 4,056,576 |
|---|---|---|
| Gregory et al. | [45] | Nov. 1, 1977 |

[54] CHEMICAL PROCESS OVER GALLIUM CATALYST CONVERTING SATURATED HYDROCARBONS TO OLEFINS

[75] Inventors: Reginald Gregory, Camberley; Alexander John Kolombos, Sutton, both of England

[73] Assignee: The British Petroleum Company Limited, London, England

[21] Appl. No.: 704,167

[22] Filed: July 12, 1976

[30] Foreign Application Priority Data

| July 17, 1975 | United Kingdom | 30012/75 |
| Nov. 20, 1975 | United Kingdom | 47829/75 |
| June 11, 1976 | United Kingdom | 24296/76 |

[51] Int. Cl.$^2$ ............................................. C07C 3/28
[52] U.S. Cl. .............................................. 260/683.3
[58] Field of Search .................................. 260/683.3

[56] References Cited

U.S. PATENT DOCUMENTS

| 3,242,069 | 3/1966 | Gladrow et al. | 208/120 |
| 3,702,886 | 11/1972 | Argauer et al. | 423/328 |
| 3,845,156 | 10/1974 | Farha | 260/680 E |
| 3,862,256 | 1/1975 | Isailingold et al. | 260/683.3 X |
| 3,887,495 | 6/1975 | Juguin et al. | 260/683.3 X |
| 3,926,781 | 12/1975 | Gale | 208/117 |
| 3,970,544 | 7/1976 | Rosinski et al. | 208/111 |
| 3,980,721 | 9/1976 | Juguin et al. | 260/683.3 X |

Primary Examiner—Delbert E. Gantz
Assistant Examiner—G. E. Schmitkons
Attorney, Agent, or Firm—Brooks, Haidt, Haffner & Delahunty

[57] ABSTRACT

This invention relates to a process for producing unsaturated hydrocarbons by dehydrogenating saturated hydrocarbons in the presence of a gallium catalyst.

12 Claims, No Drawings

CHEMICAL PROCESS OVER GALLIUM CATALYST CONVERTING SATURATED HYDROCARBONS TO OLEFINS

The present invention relates to a process for the dehydrogenation of $C_3$–$C_8$ saturated hydrocarbons to the corresponding olefins.

It has been known to use chromium oxide/alumina as catalysts in the production of olefins from open chain saturated hydrocarbons. However, such catalysts have a very short active life and need frequent regenerations to maintain activity.

It has now been found that by selecting a suitable metal as catalyst the active life over conventional catalysts may be increased.

Accordingly the present invention is a process for producing olefinic hydrocarbons from the corresponding $C_3$–$C_8$ saturated hydrocarbon feedstock comprising subjecting the feedstock to dehydrogenation in the presence of a catalyst composition comprising elemental gallium or a compound of gallium deposited on a support.

By $C_3$–$C_8$ hydrocarbon feedstock is meant here and throughout the specification feedstock containing one or more open, straight or branched chain isomers. The feedstock preferably contains one or more hydrocarbons selected from propane, butane, isobutane and pentane.

Preferred examples of gallium compounds are gallium oxide, gallium sulphate and gallium ions exhanged with the surface hydroxyls of a surface active oxide such as hydrated silica or hydrated alumina.

The amount of gallium present in such catalyst compositions may vary between 0.01 and 20%, preferably between 0.1 and 6% by weight of the total support in the catalyst composition.

Suitable examples of support for the gallium catalysts are aluminas such as eta-alumina, gamma alumina and boehmite; aluminas and silicas with or without surface hydroxyl groups which may be exchanged by ions of metals selected from gallium, aluminium, iron, and nickel; activated carbon and refractory gallium oxide. Silica supports, especially those with exchanged surface hydroxyl groups are however, preferred.

The catalyst composition of the present invention may also contain other metals such as palladium, platinum, indium, thallium, germanium, chromium, tin and/or zinc in small quantities to improve the activity thereof.

The catalyst may be prepared by impregnating the support with an aqueous solution of a soluble gallium compound, e.g. gallium nitrate. The paste so formed may be evaporated to dryness under vacuum and then pyrolysed at elevated temperature in a stream of air. Where it is desirable to use surface active silica or alumina as support, the hydroxyl groups are preferably exchanged by gallium ions.

The catalyst so prepared may be formed as a fixed bed and activated in the reactor tube itself. The activation may be carried out by purging the catalyst with a suitable gas such as nitrogen or passing air at the proposed reaction temperature.

The dehydrogenation is suitably carried out at a reaction pressure of between 1 and 20 atmospheres, preferably between 1 and 5 atmospheres.

The $C_3$–$C_8$ saturated hydrocarbon feedstock as hereinbefore described is thereafter passed over the catalyst at a temperature between 400° and 700° C, preferably between 500° and 600° C. Obviously at the lower end of the hydrocarbon feedstock range higher temperatures would be required and conversely as the number of carbon atoms in the feed increases relatively lower temperatures within the specified range can be used to obtain optimum yields. The reaction may be carried out in an inert atmosphere. By "inert atmosphere" is meant a gas which is inert under the reaction conditions, such as hydrogen. The hydrogen may be that liberated in situ during the reaction. The products of the reaction are then identified and isolated.

The dehydrogenated product may, without isolation, be directly dimerised and cyclised in one step to an aromatic compound. For example, propane may be dehydrogenated to propylene which may then be dimerised and cyclised in one step to benzene. Similarly, isobutane may be dehydrogenated to isobutene which can be dimerised and cyclised to xylenes.

Although the dehydrogenation and cyclodimerisation reactions proceed simultaneously, the product mix may be controlled by careful control of reaction conditions. That is, for a given feedstock, the dehydrogenation normally proceeds at the lower end of the specified temperature range whereas the dehydrocyclodimerisation reaction to the corresponding aromatic hydrocarbon predominates at the upper end of the same temperature range.

the steps of dimerisation and cyclisation can be carried out using the same catalyst as for dehydrogenation. That is, the saturated hydrocarbon can be converted to the cyclic product using a single set of reaction conditions over a single catalyst. Where the cyclised aromatic compound is the desired final product a mixed feed of saturated and unsaturated hydrocarbons may be used.

The invention is further illustrated with reference to the accompanying examples.

Preparation of $Ga_2O_3$/silica catalyst 4.9 g gallium nitrate, $Ga(NO_3)_3,8H_2O$ dissolved in 15 ml distilled water was added to 13 g Crosfields U 40 silica suspended in 15 ml distilled water. The mixture was evaporated to dryness in a vacuum oven overnight and heated in air at 550° for six hours to give oxide (6% wt. gallium) on silica.

EXAMPLE 1

Dehydrogenation of Propane

Propane was passed over gallium oxide (6% wt. gallium) on silica at 610° C at 6.3 sec. contact time. 18.8% wt. of the propane was converted to give 13.4% wt. of propylene at 71.3% selectivity.

EXAMPLE 2

Dehydrogenation of Isobutane

Isobutane was passed over gallium oxide (6% wt. gallium) on silica at 566° C at 5.6 sec. contact time. 24.4% wt. of butanes were converted to give 19.4% wt. of butenes at 79.5% selectivity. After 4 hours on stream, 23.9% wt. of butanes were converted to give 17.6% wt. of butenes at 73.7% selectivity.

EXAMPLE 3

When isobutane was passed over gallium oxide (1% wt. gallium) on eta-alumina at 550° C at 6.3 seconds contact time, 47.5 isobutane was converted to give 19% wt. of butenes (at 40% selectivity) and 14.4% wt. of aromatics.

EXAMPLE 4

When isobutane was passed over a gallium oxide (6% wt. gallium) on silica catalyst at a reaction temperature of 590° and a residence time of 6.2 sec., after 60 minutes on stream 65.1% of isobutane was converted. The major products (expressed as percent weight yield) were butanes (39.3%) butenes (38.7%), $C_1$–$C_3$ hydrocarbons (9.4%) and aromatics (9.2%).

EXAMPLE 5

In this example the support used was a silica containing surface hydroxyl groups exchanged with gallium ions.

When isobutane was passed over gallium (2.5% wt.) oxide/silica catalyst at a reaction temperature of 630° C and a residence time of 6.1 seconds, after 1 hour on stream 84.2% of the isobutane was converted. The major products (expressed as percent weight yield) were butenes (32.9%) at selectivity (39%), $C_1$–$C_3$ hydrocarbons (28.7%) and aromatics (18%).

We claim:

1. A process for producing olefinic hydrocarbons from the corresponding $C_3$–$C_8$ saturated hydrocarbon feedstock comprising subjecting the feedstock to dehydrogenation conditions in the presence of a catalyst composition consisting essentially of elemental gallium or a compound of gallium deposited on a support.

2. A process according to claim 1 wherein the feedstock contains one or more hydrocarbons selected from propane, butane, isobutane and pentane.

3. A process according to claim 1 wherein the gallium compound is selected from gallium oxide, gallium sulphate and gallium ions exchanged with the surface hydroxyl groups of a surface active oxide selected from hydrated alumina and hydrated silica.

4. A process according to claim 1 wherein the support is selected from an alumina, a silica, activated carbon and refractory gallium oxide.

5. A process according to claim 4 wherein the alumina is selected from eta-alumina, gamma-alumina and boehmite.

6. A process according to claim 4 wherein the alumina and silica have surface hydroxyl groups.

7. A process according to claim 6 wherein the surface hydroxyl groups are exchanged by ions of metals selected from gallium, aluminum, iron and nickel.

8. A process according to claim 1 wherein the dehydrogenation is carried out at a temperature between 400° and 700° C.

9. A process according to claim 1 wherein the dehydrogenation is carried out at a pressure of between 1 and 20 atmospheres.

10. A process according to claim 1 wherein the dehydrogenation is carried out in an atmosphere inert under the reaction conditions.

11. A process for producing olefinic hydrocarbons from the corresponding $C_3$–$C_8$ saturated hydrocarbon feedstock comprising subjecting the feedstock to dehydrogenation conditions in the presence of a catalyst composition consisting essentially of (a) elemental gallium or a compound of gallium, and (b) one or more of the metals palladium, platinum, indium, thallium, germanium, chromium, tin, and zinc deposited on a support.

12. A process according to claim 11 wherein the feedstock contains one or more hydrocarbons selected from propane, butane, isobutane and pentane.

* * * * *